(12) United States Patent
Burgess et al.

(10) Patent No.: US 11,173,261 B2
(45) Date of Patent: Nov. 16, 2021

(54) THERMISTOR FLOW SENSOR HAVING MULTIPLE TEMPERATURE POINTS

(71) Applicant: Fisher & Paykel Healthcare Limited, Auckland (NZ)

(72) Inventors: Russel William Burgess, Auckland (NZ); Houde Huang, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 259 days.

(21) Appl. No.: 16/333,168

(22) PCT Filed: Sep. 13, 2017

(86) PCT No.: PCT/NZ2017/050119
§ 371 (c)(1),
(2) Date: Mar. 13, 2019

(87) PCT Pub. No.: WO2018/052320
PCT Pub. Date: Mar. 22, 2018

(65) Prior Publication Data
US 2019/0240432 A1    Aug. 8, 2019

Related U.S. Application Data

(60) Provisional application No. 62/395,890, filed on Sep. 16, 2016.

(51) Int. Cl.
*A61M 16/00* (2006.01)
*G01F 1/698* (2006.01)
(Continued)

(52) U.S. Cl.
CPC ........ *A61M 16/0003* (2014.02); *A61M 16/00* (2013.01); *A61M 16/0066* (2013.01);
(Continued)

(58) Field of Classification Search
CPC .............. A61M 16/00; A61M 16/0003; A61M 16/0066; A61M 16/022; A61M 16/024;
(Continued)

(56) References Cited

U.S. PATENT DOCUMENTS 5,076,099 A * 12/1991 Hisanaga ................ G01F 1/698
73/204.18
2001/0027684 A1* 10/2001 Lotters .................... G01F 1/699
73/204.27
(Continued)

FOREIGN PATENT DOCUMENTS

| EP | 2055338 B1 | 2/2010 |
|---|---|---|
| WO | WO 2009/129506 A1 | 10/2009 |
| WO | WO 2018/052320 A2 | 3/2018 |

OTHER PUBLICATIONS

International Search Report in corresponding International Patent Application No. PCT/NZ2017/050119, dated Apr. 17, 2018, in 4 pages.
(Continued)

*Primary Examiner* — Joseph D. Boecker
(74) *Attorney, Agent, or Firm* — Knobbe, Martens, Olson & Bear, LLP

(57) ABSTRACT

A gases flow rate sensing system may be configured to operate in at least two different target temperature modes, based upon a measured temperature of the gases flow. In some embodiments, the gases flow sensing system may have a voltage divider containing a thermistor. The gases flow rate may be determined based upon a voltage output indicating an amount of power needed to maintain the thermistor at a target temperature as specified by the target temperature mode, and a measured temperature of the gases flow.

23 Claims, 11 Drawing Sheets

(51) Int. Cl.
  *G01F 1/00* (2006.01)
  *A61M 16/06* (2006.01)
  *A61M 16/10* (2006.01)
  *A61M 16/04* (2006.01)
  *A61M 16/16* (2006.01)

(52) U.S. Cl.
  CPC ...... *A61M 16/0096* (2013.01); *A61M 16/024* (2017.08); *A61M 16/0465* (2013.01); *A61M 16/0622* (2014.02); *A61M 16/0666* (2013.01); *A61M 16/1095* (2014.02); *A61M 16/16* (2013.01); *G01F 1/00* (2013.01); *G01F 1/698* (2013.01); *A61M 2016/0033* (2013.01); *A61M 2016/0039* (2013.01); *A61M 2205/3368* (2013.01); *A61M 2205/50* (2013.01)

(58) Field of Classification Search
  CPC ............ A61M 16/0666; A61M 16/109; A61M 16/1095; A61M 16/16; A61M 2016/0039; A61M 2205/3368; G01F 1/00; G01F 1/698
  See application file for complete search history.

(56) References Cited

U.S. PATENT DOCUMENTS

| | | | |
|---|---|---|---|
| 2009/0110379 A1* | 4/2009 | McGhin | A61M 16/026 392/485 |
| 2009/0306529 A1 | 12/2009 | Curti et al. | |
| 2011/0296910 A1* | 12/2011 | Lopez | G01F 1/69 73/204.27 |
| 2014/0116433 A1* | 5/2014 | Ghalib | A61M 16/026 128/203.14 |

OTHER PUBLICATIONS

Written Opinion in corresponding International Patent Application No. PCT/NZ2017/050119, dated Apr. 17, 2018, in 4 pages.

International Preliminary Report on Patentability in corresponding International Patent Application No. PCT/NZ2017/050119, dated Mar. 19, 2019, in 5 pages.

\* cited by examiner

THERMISTOR FLOW SENSOR HAVING MULTIPLE TEMPERATURE POINTS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

FIELD OF THE DISCLOSURE

The present disclosure relates to methods and systems for flow rate sensing in a flow therapy apparatus for delivering gas to patients.

BACKGROUND

Breathing assistance apparatuses are used in various environments such as hospital, medical facility, residential care, or home environments to deliver a flow of gas to users or patients. A breathing assistance apparatus, or a flow therapy apparatus, may include an oxygen inlet to allow delivery of supplemental oxygen with the flow of gas, and/or a humidification apparatus to deliver heated and humidified gases. A flow therapy apparatus may allow adjustment and control over characteristics of the gases flow, including flow rate, temperature, gas concentration, humidity, pressure, etc. Sensors, such as heated temperature sensing elements and/or thermistors, are used to measure these properties of the gases. This application claims priority from U.S. provisional application 62/395,890, the entire contents of which are hereby incorporated by reference.

SUMMARY

The present disclosure describes a gas flow rate sensing system which may be used to sense a gases flow rate of a gases flow. In some embodiments, the gases flow rate sensing system is configured to operate in at least two different target temperature modes, based upon a measured temperature of the flow. In some embodiments, the gases flow sensing system may comprise a voltage divider containing a thermistor, wherein the gases flow rate may be determined based upon a voltage output indicating an amount of power needed to maintain the thermistor at a target temperature as specified by the target temperature mode, and a measured temperature of the gases flow.

A breathing assistance apparatus that provides a flow of gases to a patient may comprise at least one gases flow path configured to direct the flow of gases to the patient. The breathing assistance apparatus may further comprise a gases flow inlet configured to receive the flow of gases from a gases flow source. The breathing assistance apparatus may further comprise a temperature sensor configured to measure a temperature of the gases flow. The breathing assistance apparatus may further comprise a gases flow rate sensing system configured to measure a gases flow rate of the flow of gases, wherein the gases flow rate sensing system is configured to operate in at least two different temperature modes, based upon the measured temperature of the gases flow.

The gases flow source may comprise a blower.

The temperature sensor and/or the gases flow rate sensing system may be upstream of the blower.

The temperature sensor and/or the gases flow rate sensing system may be comprised within a sensor assembly having a housing. The sensor assembly may be located in a sensor zone within an inlet flow path prior to the blower.

The temperature sensor and/or the gases flow rate sensing system may be downstream of the blower.

The blower may be comprised within a blower/sensor module.

The blower/sensor module may be removable and configured for insertion into a housing of the apparatus.

The blower/sensor module may be non-removable and configured for insertion into a housing of the apparatus.

The blower/sensor module may comprise a sensing circuit board.

At least a portion of the gases flow rate sensing system may be on or within the sensing circuit board.

The breathing assistance apparatus may be a Continuous Positive Airway Pressure (CPAP) apparatus. The breathing assistance apparatus may deliver a noninvasive ventilation (NIV) flow. The breathing assistance apparatus may deliver a nasal high flow (NHF) flow of gases.

The breathing assistance apparatus may further comprise a humidifier.

The gases flow path may be a heated respiratory tube.

The breathing assistance apparatus may further comprise a patient interface selected from at least one of: a face mask, a nasal mask, a nasal pillows mask, a tracheostomy interface, a nasal cannula, or endotracheal tube.

The gases flow rate sensing system may comprise a thermistor circuit.

The gases flow rate sensing system may be configured to change from a first temperature mode to a second temperature mode in response to the measured temperature of the gases flow meeting a predetermined threshold.

The thermistor circuit may comprise a voltage divider. The voltage divider may comprise at least a first arm and a second arm Changing a target temperature mode of the thermistor circuit may comprise changing a resistance value of an arm of the voltage divider.

Changing a resistance value of an arm of the voltage divider may comprise connecting or disconnecting or bypassing or not bypassing a resistor to the arm of the voltage divider. Changing a resistance value of an arm of the voltage divider may comprise connecting the resistor to the arm of the voltage divider. Changing a resistance value of an arm of the voltage divider may comprise bypassing the resistor to the arm of the voltage divider.

The breathing assistance apparatus may comprise a buffer stage between the voltage divider and a power supply.

The buffer stage may comprise a transistor.

The voltage divider may be driven by dual power supplies.

The gases flow rate sensing system may be configured to operate in two different temperature modes, based upon the measured temperature of the gases flow.

The gases flow rate sensing system may be configured to operate in more than two different temperature modes.

A system for measuring a flow rate of a flow of gases may comprise a thermistor circuit including a thermistor. The thermistor circuit may be configured to produce a voltage output and to operate in at least a first temperature mode and a second target temperature mode. The system may further comprise a temperature sensor configured to measure a gases flow temperature. The system may further comprise a controller coupled to the temperature sensor and the thermistor circuit, wherein the controller is configured to adjust the thermistor circuit to change between the at least first and second target temperature modes, in response to changes in the measured gases flow temperature.

Thermistor circuit may be a constant temperature circuit.

The thermistor may be positioned to be within the flow of gases.

The controller may be configured to adjust the thermistor circuit to change between at least the first and second target temperature modes by connecting or bypassing a first resistor within the thermistor circuit. The controller may be configured to adjust the thermistor circuit to change between at least the first and second target temperature modes by connecting the first resistor within the thermistor circuit. The controller may be configured to adjust the thermistor circuit to change between at least the first and second target temperature modes by bypassing the first resistor within the thermistor circuit.

The thermistor circuit may be arranged as a Wheatstone bridge configuration comprising a first voltage divider arm and a second voltage divider arm, wherein the thermistor may be located on the second voltage divider arm.

The first resistor may be located on the first voltage divider arm.

The connecting or bypassing of the first resistor may comprise using a switch to disconnect or connect a low resistance path in parallel with the first resistor. The connecting of the first resistor may comprise using the switch to disconnect the low resistance path in parallel with the first resistor. The bypassing of the first resistor may comprise using the switch to connect the low resistance path in parallel with the first resistor.

A resistance value of a second resistor located on the second arm with the thermistor in the Wheatstone Bridge may be configured to correspond to a geometric mean of a first thermistor resistance of the thermistor corresponding to the first target temperature mode and a second thermistor resistance of the thermistor corresponding to the second target temperature mode.

The first resistor may be located on a lower part of the first voltage divider arm and may be configured to have a resistance such that when the first resistor is bypassed, a first ratio between an upper part and the lower part of the first voltage divider arm substantially matches a second ratio between the second resistor to the first thermistor resistance, and when the first resistor is connected, the first ratio substantially matches a third ratio between the second resistor to the second thermistor resistance.

The Wheatstone bridge configuration may further comprise a buffer stage located between the first and second voltage divider arms and a power supply.

The buffer stage may comprise a transistor, a gate of the buffer stage connected to an output of an op-amp of the Wheatstone bridge.

The Wheatstone bridge may be driven by at least two power supplies.

The voltage output of the thermistor circuit may be configured to correspond to a first voltage range when operating in either the first temperature mode or the second temperature mode.

The first voltage range may be between about 1V to about 38V, or 2V to 30V, or 3V to 25V or 4V to 20V. The first voltage range may be between about 5V to about 15V.

The voltage output of the thermistor circuit may be scaled and shifted from the first voltage range to a second voltage range.

The scaling and shifting may be performed by an operational-amplifier (op-amp) circuit.

The second voltage range may be substantially between about 0V to about 5V, or 0V to 4V or 0V to 3.5V. The second voltage range may be substantially between about 0V to about 3.3V.

The voltage output of the thermistor circuit may indicate an amount of power required to keep the thermistor at a constant temperature corresponding to either the first target temperature mode or the second target temperature mode.

The gases flow rate may be determined based upon the voltage output and the measured gases flow temperature.

The thermistor circuit may provide a different range of voltage outputs for the each of the first and second temperature modes.

The voltage output of the thermistor circuit may be scaled and shifted by a scaling and shifting mechanism, wherein the scaling and shifting mechanism may be modified based upon the temperature mode that the thermistor circuit is operating in such that an output voltage range of the scaling and shifting mechanism may be substantially the same in either the first or second target temperature mode.

The scaling and shifting mechanism may be an op-amp circuit.

The op-amp circuit may be modified by connecting or bypassing a resistor.

The output voltage range of the scaling and shifting mechanism may be substantially between about 0V and about 5V, or 0V to 4V or 0V to 3.5V. The output voltage range of the scaling and shifting mechanism may be substantially between about 0V and about 3.3V.

The first and second target temperature modes may comprise a lower temperature mode and a higher temperature mode, and wherein the controller may be configured to switch the thermistor circuit from operating in the lower temperature mode to the higher temperature mode when the measured gases flow temperature is higher than a first threshold value.

The controller may be configured to switch the thermistor circuit from operating in the higher temperature mode to the lower temperature mode when the measured gases flow temperature is lower than a second threshold value.

The first threshold value may be higher than the second threshold value.

The controller may be configured to be unable to adjust the thermistor circuit between the first and second target temperature modes for a pre-determined period of time after a previous adjustment.

The first and second target temperature modes may correspond respectively to between about 50° C. to about 70° C., and between about 90° C. to about 110° C. The first and second target temperature modes may correspond respectively to between about 60° C. to about 67° C., and between about 95° C. to about 105° C. The first and second target temperature modes may correspond respectively to about 66° C. and about 100° C.

The first and second target temperature modes may be associated with gases flow temperature ranges of between about 0° C. to about 60° C., and between about 20° C. to about 100° C. respectively. The first and second target temperature modes may be associated with gases flow temperature ranges of between 0° C. to about 50° C., and between about 25° C. to about 85° C. respectively. The first and second target temperature modes may be associated with gases flow temperature ranges of about 0° C. to about 40° C. and about 30° C. to about 70° C. respectively The controller may be a microcontroller.

The controller may comprise a comparator circuit.

The controller may be configured to adjust the thermistor circuit to change between more than two different target temperature modes, in response to changes in the measured gases flow temperature A system for measuring a speed or velocity of a gases flow may comprise a thermistor circuit comprising a thermistor, the thermistor circuit having a plurality of different target temperature modes. The thermistor circuit may be configured to output a range of output voltages, the range of output voltages being the same for each of the plurality of temperature modes.

The system may comprise a temperature sensor configured to measure a gases flow temperature.

The output voltages output by the thermistor may represent a power draw of the thermistor circuit and indicate a speed or velocity of the gases flow.

The output voltages output by the thermistor represent a power draw of the thermistor circuit and indicate a flow rate of the gases flow.

The thermistor circuit may have more than two different target temperature modes.

The thermistor circuit may be configured to measure gases flow rates of between about 0 L/min to about 200 L/min. The thermistor circuit may be configured to measure gases flow rates of between about 0 L/min to about 150 L/min. The thermistor circuit may be configured to measure gases flow rates of between about 0 L/min to about 100 L/min.

The system may further comprise a blower.

The thermistor circuit may be upstream of the blower.

The thermistor circuit may be downstream of the blower.

The blower may be configured to provide a high flow therapy to a patient.

The blower may be comprised within a blower/sensor module.

The blower/sensor module may be removable and configured for insertion into a housing of the system.

The blower/sensor module may be non-removable from a housing of the system.

The blower/sensor module may comprise a sensing circuit board.

At least a portion of the thermistor circuit may be on or within the sensing circuit board.

The system may further comprise a patient breathing conduit configured to be coupled to a gases flow outlet of the system at one end of the conduit and to a patient interface at another end of the conduit.

The patient interface may be a nasal cannula, a full face mask, a nasal mask, an tracheostomy interface, a nasal pillows mask, or an endotracheal tube.

The patient breathing conduit may comprise a heater wire configured to heat gases passing through the conduit.

The system may further comprise a humidifier configured to humidify the gases flow to a patient.

DETAILED DESCRIPTION

Figure 1A:
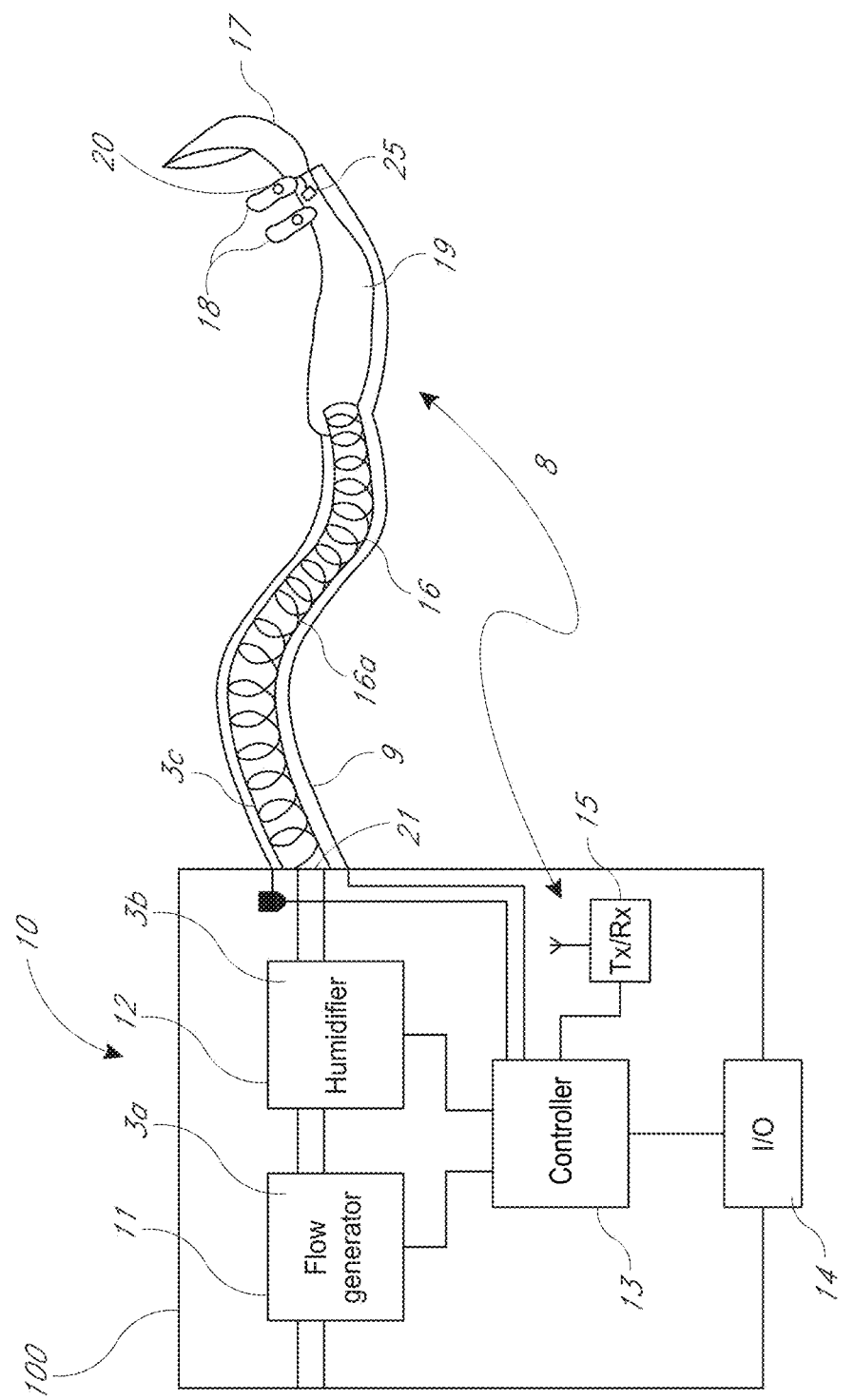
FIG. 1A shows in diagrammatic form a breathing assistance apparatus in the form of a flow therapy apparatus.

A flow therapy apparatus 10 is shown in FIG. 1A. The apparatus 10 can comprise a main housing 100 that contains a flow generator 11 in the form of a motor/impeller arrangement (for example, a blower), an optional humidifier 12, a controller 13, and a user interface 14 (comprising, for example, a display and input device(s) such as button(s), a touch screen, or the like). The controller 13 can be configured or programmed to control the components of the apparatus, including but not limited to: operating the flow generator 11 to create a flow of gas (gases flow) for delivery to a patient, operating the humidifier 12 (if present) to humidify and/or heat the generated gases flow, receiving user input from the user interface 14 for reconfiguration and/or user-defined operation of the apparatus 10, and outputting information (for example on the display) to the user. The user can be a patient, healthcare professional, or anyone else interested in using the apparatus. As used herein, a "gases flow" can refer to any flow of gases that may be used in the breathing assistance or respiratory device, such as a flow of ambient air, a flow comprising substantially 100% oxygen, a flow comprising some combination of ambient air and oxygen, and/or the like.

A patient breathing conduit 16 is coupled at one end to a gases flow outlet 21 in the housing 100 of the flow therapy apparatus 10. The patient breathing conduit 16 is coupled at another end to a patient interface 17 such as a nasal cannula with a manifold 19 and nasal prongs 18. Additionally, or alternatively, the patient breathing conduit 16 can be coupled to a face mask, a nasal mask, a nasal pillows mask, an endotracheal tube, a tracheostomy interface, and/or the like. The gases flow, which may be humidified, that is generated by the flow therapy apparatus 10, is delivered to the patient via the patient conduit 16 through the cannula 17. The patient conduit 16 can have a heater wire 16a to heat gases flow passing through to the patient. The heater wire 16a can be under the control of the controller 13. The patient conduit 16 and/or patient interface 17 can be considered part of the flow therapy apparatus 10, or alternatively peripheral to it. The flow therapy apparatus 10, breathing conduit 16, and patient interface 17 together can form a flow therapy system.

The controller 13 can control the flow generator 11 to generate a gases flow of the desired flow rate. The controller 13 can also control a supplemental oxygen inlet to allow for delivery of supplemental oxygen, the humidifier 12 (if present) to humidify the gases flow and/or heat the gases flow to an appropriate level, and/or the like. The gases flow is directed out through the patient conduit 16 and cannula 17 to the patient. The controller 13 can also control a heating element in the humidifier 12 and/or the heating element 16a in the patient conduit 16 to heat the gas to a desired temperature for a desired level of therapy and/or level of comfort for the patient. The controller 13 can be programmed with or can determine a suitable target temperature of the gases flow.

Operation sensors 3a, 3b, 3c, such as flow, temperature, humidity, and/or pressure sensors can be placed in various locations in the flow therapy apparatus 10. In some embodiments, additional sensors (for example, sensors 20, 25) may be placed in various locations on the patient conduit 16 and/or cannula 17 (for example, there may be a temperature sensor at or near the end of the inspiratory tube). Output from the sensors can be received by the controller 13, to assist the controller in operating the flow therapy apparatus 10 in a manner that provides suitable therapy. In some configurations, providing suitable therapy includes meeting a patient's peak inspiratory demand. The apparatus 10 may have a transmitter and/or receiver 15 to enable the controller 13 to receive signals 8 from the sensors and/or to control the various components of the flow therapy apparatus 10, including but not limited to the flow generator 11, humidifier 12, and heater wire 16a, or accessories or peripherals associated with the flow therapy apparatus 10. Additionally, or alternatively, the transmitter and/or receiver 15 may deliver data to a remote server or enable remote control of the apparatus 10.

In some embodiments, the flow therapy apparatus 10 may comprise a high flow therapy apparatus. As used herein, "high flow" therapy may involve the administration of gas to the airways of a patient at a relatively high flow rate. For example, for adults, the flow rate can be at least about 15 L/min, or about 20 L/min, or about 25 L/min, or about 30 L/min, or about 40 L/min, or about 50 L/min, or up to about 150 L/min. For children and infants, the flow rate may be about 1 L/min, or about 2 L/min, and up to about 25 L/min, or about 3 L/min, or about 5 L/min, or about 10 L/min, or about 15 L/min, or about 20 L/min. High flow therapy may be administered to the nares of a user and/or orally, or via a tracheostomy interface. High flow therapy may deliver gases to a user at a flow rate at or exceeding the intended user's peak inspiratory flow requirements. The high flow of gases reaching the patient's airways can be beneficial for flushing out the patient's airways, which can reduce the volume of anatomical dead space. High flow therapy can often be delivered with a non-sealing patient interface such as, for example, a nasal cannula. The nasal cannula may be configured to deliver breathing gases to the nares of a user at a flow rate exceeding the intended user's peak inspiratory flow requirements.

The term "non-sealing patient interface" as used herein can refer to an interface providing a pneumatic link between an airway of a patient and a gases flow source (such as from flow generator 11) that does not completely occlude the airway of the patient. Non-sealed pneumatic link can comprise an occlusion of less than about 95% of the airway of the patient. The non-sealed pneumatic link can comprise an occlusion of less than about 90% of the airway of the patient. The non-sealed pneumatic link can comprise an occlusion of between about 40% and about 80% of the airway of the patient. The airway can include one or more of a nare or mouth of the patient.

Figure 1B:
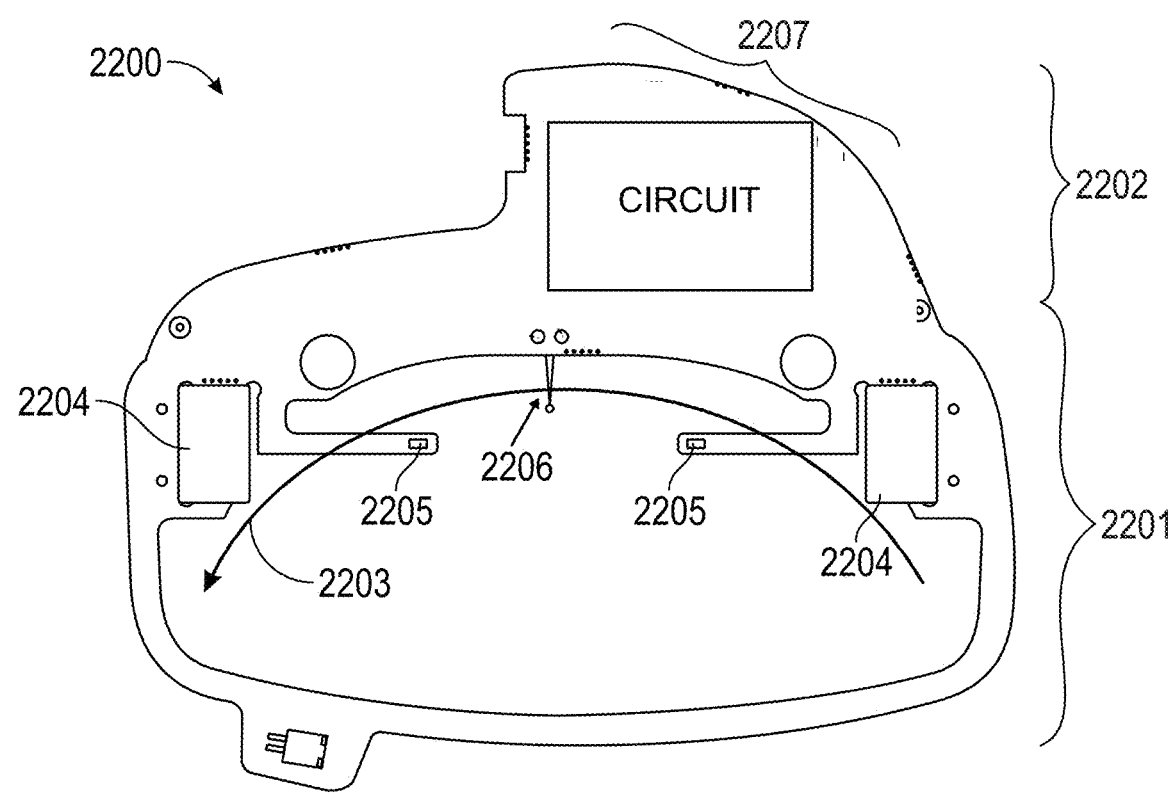
FIG. 1B illustrates an example of a sensing circuit board including a flow rate sensor that may be used in a breathing assistance apparatus.

Turning to FIG. 1B, a sensing circuit board 2200 that can be implemented in the flow therapy apparatus 10 described above is shown. Specifically, the flow therapy apparatus 10 can include a recess for housing a motor/sensor module. The motor/sensor module can include the flow generator or blower, which can entrain room air into an inlet port of the blower. The inlet port can optionally include a valve through which a pressurized gas may enter the flow generator or blower. The valve can control a flow of oxygen into the flow generator blower. The valve can be any type of valve, including a proportional valve or a binary valve.

The blower can operate at a motor speed of greater than about 1,000 RPM and less than about 30,000 RPM, greater than about 2,000 RPM and less than about 21,000 RPM, or between any of the foregoing values. Operation of the blower can mix the gases entering the blower through the inlet port. Using the blower as the mixer can decrease the pressure drop that would otherwise occur in a system with a separate mixer, such as a static mixer comprising baffles, because mixing requires energy.

The mixed air can exit the blower through a conduit and enter a flow path in a sensor chamber of the motor/sensor module. The sensing circuit board 2200 can be positioned in the sensor chamber such that the sensing circuit board 2200 is at least partially immersed in the flow of gases. At least some of the sensors on the sensing circuit board 2200 can be positioned within the flow of gases to measure gas properties within the flow. After passing through the flow path 2006 in the sensor chamber, the gases can exit to the humidifier 12 described above.

The sensing circuit board 2200 can be a printed sensing circuit board (PCB). Alternatively, the circuit on the board 2200 can be built with electrical wires connecting the electronic components instead of being printed on a circuit board. At least a portion of the sensing circuit board 2200 can be mounted outside of a flow of gases. The flow of gases can be generated by the flow generator 11 described above. The sensing circuit board 2200 can comprise ultrasonic transducers 2204. The sensing circuit board 2200 can comprise one or more of thermistors 2205. The thermistors 2205 can be configured to measure a temperature of the gases flow. The sensing circuit board 2200 can comprise a thermistor flow rate sensor 2206. The sensing circuit board 2200 can comprise other types of sensors, such as humidity sensors including humidity only sensors to be used with a separate temperature sensor and combined humidity and temperature sensors, sensors for measuring barometric pressure, sensors for measuring differential pressure, and/or sensors for measuring gauge pressure. The thermistor flow rate sensor 2206 can comprise hot wire anemometer, such as a platinum wire, and/or a thermistor, such as a negative temperature coefficient (NTC) or positive temperature coefficient (PTC) thermistor. Other non-limiting examples of the heated temperature sensing element include glass or epoxy-encapsulated or non-encapsulated thermistors. The thermistor flow rate sensor 2206 can be configured to measure flow rate of the gases by being supplied with a constant power, or be maintained at a constant sensor temperature or a constant temperature difference between the sensor and the flow of gases.

The sensing circuit board 2200 can comprise a first portion 2201 and a second portion 2202. The first portion 2201 can be positioned to be within the flow path 2006 of the gases, whereas the second portion 2202 can be positioned to be outside the flow path 2006 of the gases. The direction of the flow of gases is indicated in FIG. 1B by the arrow 2203. The direction of the flow of gases can be a straight line, or curved in shown in FIG. 1B.

Positioning the one or more of thermistors 2205 and/or the thermistor flow rate sensor 2206 downstream of the combined blower and mixer can take into account heat supplied to the gases flow from the blower. Also, immersing the temperature-based flow rate sensors in the flow path can increase the accuracy of measurements because the sensors being immersed in the flow can more likely to be subject to the same conditions, such as temperature, as the gases flow and therefore provide a better representation of the gases characteristics.

An example of a flow therapy apparatus is disclosed in International Application No. PCT/NZ2016/050193, titled "Flow Path Sensing for Flow Therapy Apparatus", filed on Dec. 2, 2016, which is hereby incorporated by reference in its entirety.

Flow Measurement Using a Thermistor

In many breathing assistance apparatuses and other apparatuses configured to deliver a flow of gas, it is often necessary to be able to measure a flow rate (for example, a speed or velocity of the flow of gas) using a sensing system comprising one or more sensors, such as a thermistor or an ultrasonic sensor arrangement. For example, in the context of a non-sealed breathing assistance apparatus, flow rate may be measured in order to determine a breath cycle of the patient.

In some embodiments, the gases flow rate may be measured using at least two different types of sensors. For example, a first type of sensor may be able to measure flow rate with better short-term or local accuracy (for example, detecting rapid, breath by breath changes in flow rate) but poorer long-term accuracy (for example, due to the accumulation of small errors), while a second type of sensor may be able to measure flow rate with poorer local accuracy (for example, due to local noise) but better average accuracy. Output readings from both the first and second types of sensors may be combined to determine a more accurate flow measurement. For example, in some embodiments, a previously determined flow rate and one or more outputs from the second type of sensor can be used to determine a predicted current flow rate. The predicted current flow rate may then be updated using one or more outputs from the first type of sensor, in order to calculate a final flow rate.

The first type of sensor may comprise an ultrasonic sensor assembly (for example, the ultrasonic sensors 2204 in FIG. 1B). The second type of sensor can be based on various methods of hot wire anemometry, which can measure a flow rate by monitoring convection-cased heat transfer between a flow of gases and the sensor. As described above, examples of hot wire anemometry sensors can include a hot wire anemometer or a thermistor (hereinafter also referred to as a "thermistor flow sensor"), such as the thermistor flow rate sensor 2006 as shown in FIG. 1B. Although FIG. 1B illustrates the thermistor flow rate sensor 2206 inside a sensing chamber downstream of the blower with the advantages described above, in some embodiments, the thermistor flow sensor can also be located upstream of the blower. The apparatus can have an inlet flow path prior to the blower. The inlet flow path can be defined by three main zones, which are an inlet zone, a sensor zone, and a transition zone. The inlet zone can be an initial portion of the inlet flow path. The sensing zone can be between the inlet zone and the transition zone. The transition zone can include an exit port coupled to the blower. The thermistor flow sensor can be located in the sensor zone of the inlet flow path prior to the blower.

Hot wire anemometry can measure a flow rate by monitoring heat transfer between a flow of gases and the sensor. As described above, either a hot wire anemometer or a thermistor can be supplied with a constant power, or be maintained at a constant sensor temperature or a constant temperature difference between the sensor and the flow of gases. For example, under the constant temperature mode, which is what the present disclosure is concerned with a thermistor flow sensor may operate by running a thermistor at a constant target temperature within the flow when the gases flows around and past the thermistor, and measuring an amount of power required to maintain the thermistor at the target temperature. In some embodiments, the target temperature can be configured to be higher than a temperature of the gases flow, such that the higher the flow rate, the more power will be required to maintain the thermistor at the target temperature.

Figure 2:
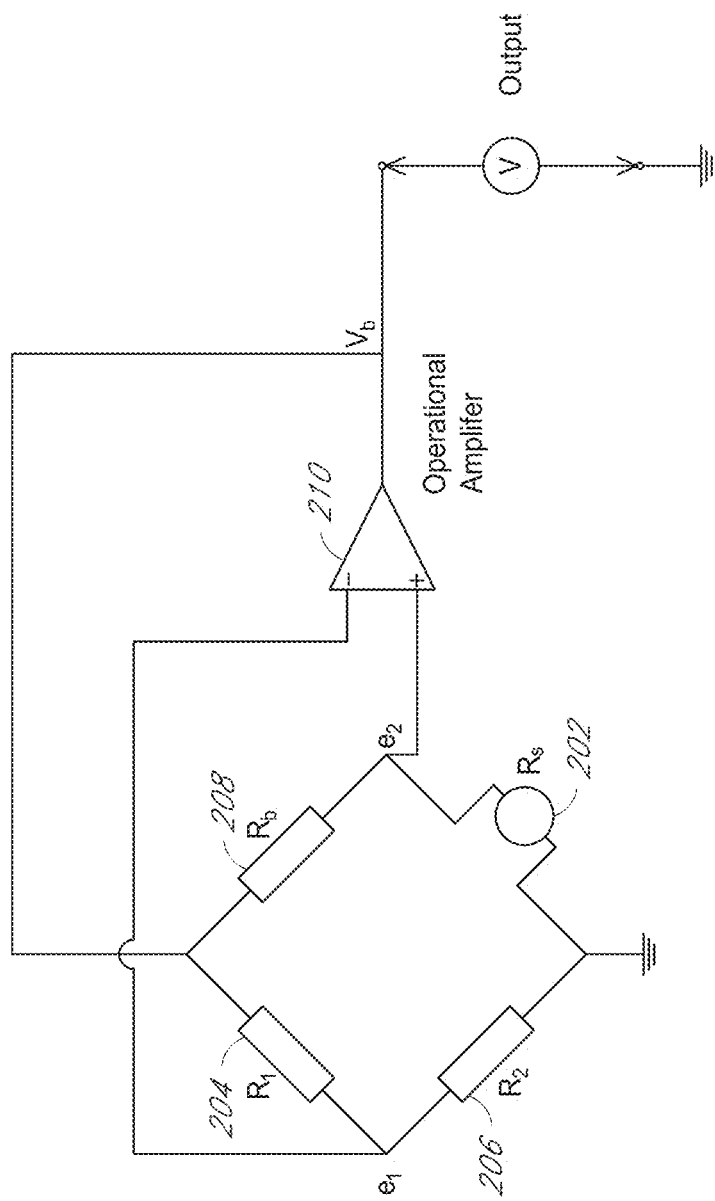
FIG. 2 illustrates an example of a thermistor circuit that may be used in a thermistor flow sensor.

FIG. 2 illustrates an example of a thermistor circuit that may be used in a thermistor flow sensor, in accordance with some embodiments. In some embodiments, the thermistor circuit 200 may be a constant temperature circuit, such as a Wheatstone bridge circuit for maintaining a constant target temperature for the thermistor 202. Thermistor 202 has a resistance $R_s$ that is dependent upon its temperature more so than in standard resistors. In some embodiments, the thermistor 202 has a resistance with a negative temperature coefficient. For example, the higher the temperature of the thermistor, the lower the resistance $R_s$ of thermistor 202 will be.

In some embodiments, the thermistor circuit 200 comprises a bridge circuit. The bridge circuit can have a first arm with a first voltage divider formed using resistors 204 and 206 having resistances $R_1$ and $R_2$, which sets up a reference voltage $e_1$. The bridge circuit can have a second arm with a second voltage divider formed from the thermistor 202 and a resistor 208 having a resistance of $R_b$ that sets up a second voltage $e_2$. The op-amp 210 may provide feedback to keep the thermistor circuit 200 in balance, such that the voltage $e_1$ is equal to the voltage $e_2$.

With the appropriate biasing and circuit construction, the thermistor circuit 200 may produce a constant target temperature on the thermistor 202. For example, if the thermistor 202 were to be cooled by a gases flow (thus increasing resistance $R_s$ and consequently voltage $e_2$), the op-amp 210 would function to provide greater power to the bridge circuit in order to keep the temperature of the thermistor 202 constant. The voltage $V_b$ being provided in the feedback loop of the op-amp 210 is indicative of the amount of power provided. Thus, the amount of power being delivered can be determined by tracking $V_b$. The measured voltage may be received by a controller of a sensing system of the breathing assistance apparatus (for example, controller 13) in order to calculate a gases flow rate. In some embodiments, the voltage is fed into an ADC associated with the controller (for example, an ADC port of the controller) to convert the analog voltage signal into a digital signal for processing of the controller. In some embodiments, a voltage drop across the thermistor 202 may be read to determine the amount of power being delivered. In some embodiments, the controller configured to control the thermistor flow sensor may be a microcontroller.

The target temperature for the thermistor circuit 200 can be selected by selecting the resistances in the circuit (for example, resistors 204, 206, and 208). For example, since it is inherent from the circuit 200 that voltages $e_1=e_2$, the resistance of the thermistor 202$R_s$ may be calculated as:

$$\frac{R_2}{R_1} = \frac{R_s}{R_b}$$

$$R_s = \frac{R_b \times R_2}{R_1}$$

As such, the resistances of resistors 204, 206, and 208 may be selected based upon a desired resistance $R_s$ corresponding to a desired target temperature for thermistor 202.

In some embodiments, the voltage from the thermistor circuit 200 (for example, voltage $V_b$) may have a different range compared to the voltage that can be accepted at the controller (for example, the voltage range of an ADC port of the controller). As such, the voltage may be fed into a differential op-amp configuration, allowing for the voltage to be scaled and/or shifted to better match the voltage range of the ADC, allowing for substantially the entire range of the ADC to be used. This may allow for greater resolution and more accurate power readings. The resulting signal from the differential op-amp may be delivered to an ADC port of the controller to be read.

Figure 3:
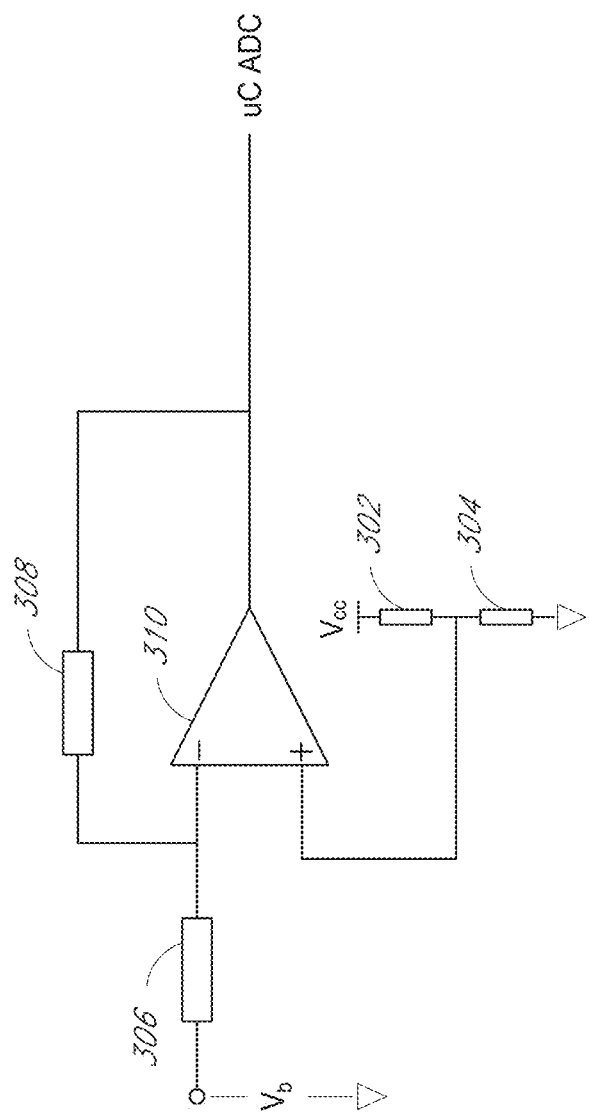
FIG. 3 illustrates a differential op-amp circuit that may be used in some embodiments.

FIG. 3 illustrates a differential op-amp circuit 300 that may be used in some embodiments. By selecting appropriate values for resistors 302, 304, 306, and 308, the incoming signal ($V_b$) may be DC shifted and scaled by op-amp 310. For example, if the output range of $V_b$ is known, the differential op-amp circuit 300 can be configured to shift and/or scale the $V_b$ signal to cover substantially the entire possible range of values of the ADC input of the controller. By allowing for substantially the entire voltage range of the ADC to be used, the resolution of the system in reading power consumption (and therefore gases flow) may be improved.

The signal from the op-amp 310 may be delivered to an ADC port of the controller to be read by the controller. In addition, the controller may receive readings from a temperature sensor for sensing a temperature of the gases flow. By determining the power delivered to the thermistor 202 (based upon the voltage $V_b$), a power lost through the thermistor 202 due to the gases flow passing over the thermistor 202 can be determined. Since the temperature of the gases flow is known (using the temperature sensor), an amount of gases flow passing over the thermistor 202 (and hence a gases flow rate) can be determined.

Flow Temperature and Flow Sensor Resolution

In some embodiments, a primary purpose of a thermistor flow sensor is to be able to measure a flow accurately (as opposed to measuring quickly, which may be performed using, for example, an ultrasonic sensor arrangement). However, where there is a large range of possible flow temperatures, the resolution requirements of the thermistor flow sensor may become stretched or squashed when the difference between the gases flow temperature and the thermistor target temperature is too small or too great.

For example, when the gases flow temperature is close to the target temperature of the thermistor, the power requirement necessary to maintain the thermistor target temperature may be very small. For example, for a thermistor maintaining a target temperature of about 66° C., if the temperature of the gases flow was about 64° C., there would be very little power drawn to maintain the thermistor target temperature, regardless of the speed or density of the gases flow. As such, the thermistor flow sensor may need to be extremely sensitive in order to be able to detect minute changes in the power requirement.

If the difference between the gases flow temperature and the thermistor target temperature is large (for example, the thermistor target temperature is about 100° C., while the gases flow temperature is about 5° C.), slight changes in the gases flow rate may drastically alter the amount of power required to maintain the thermistor target temperature. This may require the ADC and op-amp to cover a large range of power values, sacrificing detailed resolution. In addition, if the temperature difference is too large, it may be possible that the power draw required to maintain the thermistor at the target temperature becomes greater than an amount of power that can be supplied. Furthermore, self-convection can occur when there is a large difference between the temperature of the flow and the target temperature, which may make it difficult to accurately calculate flow rate. For example, when the thermistor flow sensor has a high target temperature relative to the gases flow temperature, convection may occur above the thermistor creating additional movement of gases, resulting in distortions in the reading of the thermistor flow sensor.

Therefore, as discussed above, it may be undesirable for the difference between the gases flow temperature and the thermistor target temperature to be too large or too small. In some embodiments, the thermistor target temperature may be associated with a desired gases flow temperature range, indicating a range of gases flow temperatures wherein the differences between the thermistor target temperature and the gases flow temperatures are not too small or too large.

One way to overcome a large temperature range of the gases is to use a hot wire anemometer or a thermistor that maintains a constant temperature difference between the sensor temperature and gas temperature. Hot wire anemometers that can maintain a constant temperature difference can be expensive, prone to damage and/or malfunction, and/or need to be replaced frequently. A thermistor can be cheaper and more durable than hot wires. However, maintaining a constant temperature difference on the thermistor can make the compensation circuit of the thermistor flow sensor complicated and inaccurate. Another way to overcome a large temperature range of the gases, as described in the present disclosure, is to maintain a plurality of (for example, two, three, or more) constant temperatures on a thermistor of the flow rate sensor. The plurality of different temperatures can allow the thermistor flow rate sensor to be accurate across the large temperature range of the gases.

Dual Temperature Thermistor Circuit

In some embodiments, in order to avoid the difference between the gases flow temperature and the thermistor target temperature being in an undesirable range (for example, the difference being too great or too small), a thermistor circuit may be configured to operate at multiple different target temperatures (may also be referred to as target temperature modes or constant temperature modes). For example, the thermistor circuit may be configured to be able to switch between two different target temperatures, such that the temperature of the gases flow will always fall within a certain range relative to one of the two target temperatures (for example, not too close but not too far). For example, in an embodiment, the thermistor circuit may be configured to operate at a first target temperature of about 66° C., associated with a desirable flow temperature range of between about 0° C. and about 40° C., and a second target temperature of about 100° C., associated with a desirable flow temperature range of between about 30° C. and about 70° C. While the subsequent disclosure is directed primarily to thermistor circuits having two different target temperatures, it is understood that in other embodiments, the thermistor circuit may be associated with more than two different operating temperatures, such as three or four, or five or six, etc.

Figure 4A:
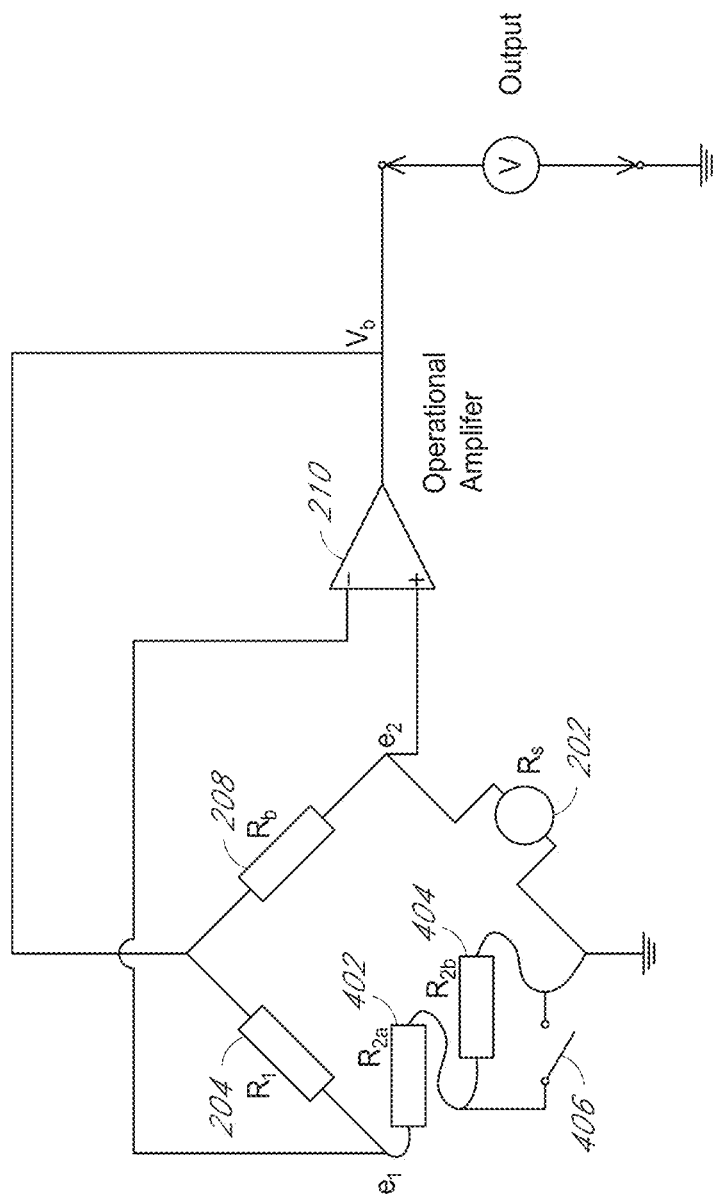
FIG. 4A illustrates a modified thermistor circuit configured to operate at two different target temperatures.

FIG. 4A illustrates a modified thermistor circuit 400 configured to operate at two different target temperatures, in accordance with some embodiments. Thermistor circuit 400 may be similar to thermistor circuit 200, except that resistor 206 may be replaced with two different resistors 402 and 404 having respective resistances $R_2a$ and $R_2b$. In some embodiments, resistors 402 and 404 may be connected in series. At least one of the two resistors (for example, resistor 404) may be bypassed via a switch 406. When connected, the switch 406 may provide a path of low (ideally zero) resistance in parallel to the resistor 404, essentially "short circuiting" the resistor 404. As such, the reference voltage $e_1$ may be altered based upon whether the resistor 404 is bypassed or not. In other embodiments, the switch 406 may be placed in other locations in the Wheatstone bridge in order to change a ratio of resistance in the two arms of the circuit (for example, by switching in or out $R_1$ or $R_b$).

In some embodiments, the switch 406 is not a physical switch, but may instead be a bi-polar junction thermistor (BJT) or other type of switch that can be electronically switched on or off by the controller in order to connect or bypass resistor 406. In some embodiments, the switch 406 and resistor 404 could alternatively be replaced with a voltage controlled resistor, such as a field effect transistor (FET) or JFET operated in the ohmic region. In this manner multiple values of resistance 404 may be selected by varying the control voltage. In some embodiments, the control voltage may be configured to switch between one or more set values, such that the value of resistance 404 is able to be switched between one or more set resistance values.

Figure 4C:
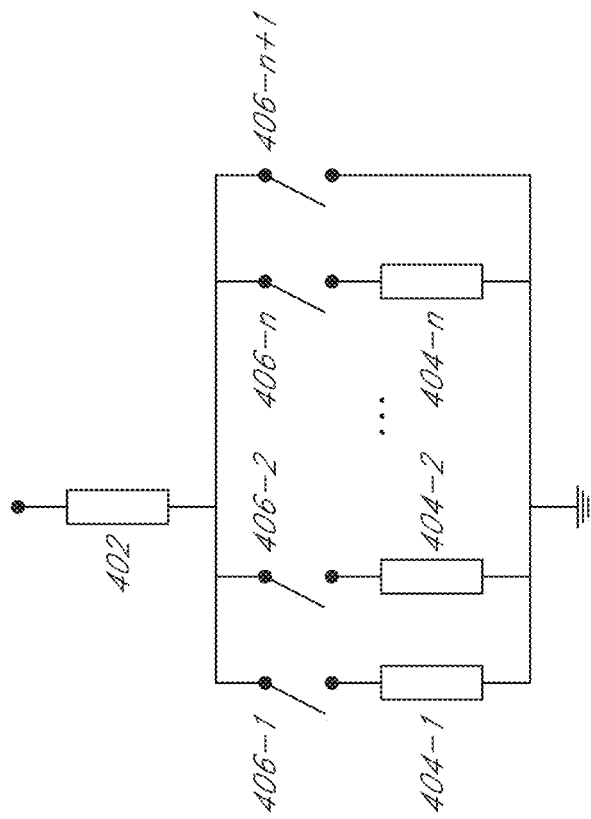
FIGS. 4B and 4C illustrate alternate resistor arrangements in a thermistor circuit configured to operate at a plurality of different target temperatures.
Figure 4B:
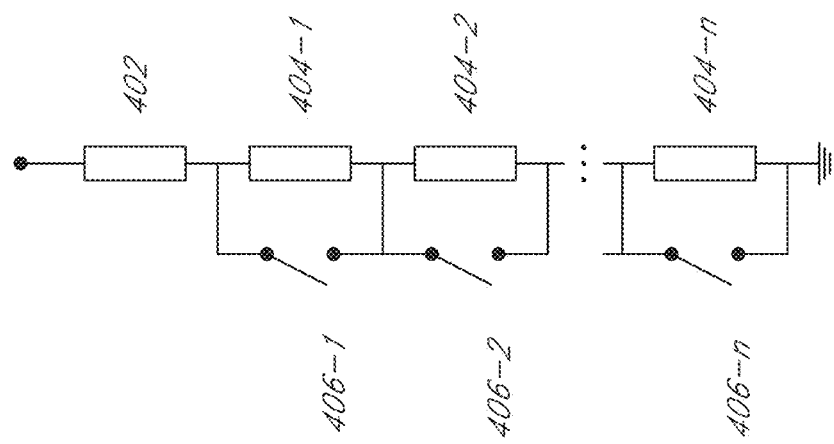

In some embodiments, more than two different temperature modes may be implemented by increasing a number of different possible resistances that may be achieved. For example, FIGS. 4B and 4C illustrate alternative configurations for resistors 402, 404, and switch 406 for implementing a larger number of different resistance values. FIG. 4B illustrates the resistor 404 comprising a plurality of resistors 404-1 through 404-n. The resistors 404-1 through 404-n can be arranged in a series arrangement. FIG. 4C illustrates the resistor 404 comprising a plurality of resistors 404-1 through 404-n and the switch 406 comprising a plurality of switches 406-1 through 406-n. The resistors 404-1 through 404-n can be arranged in parallel. The switches 406-1 through 406-n can each allow for a corresponding resistor 404-1 through 404-n to be connected as part of the circuit or to be bypassed. By opening and closing different combinations of switches 406-1 through 406-n to connect or bypass resistors 404-1 through 404-n, different resistances may be achieved. The different resistances may correspond to different temperature modes. In some embodiments with a parallel arrangement, an additional switch 406-n+1 may be used in order to bypass all resistors 404-1 through 404-n.

Figure 4E:
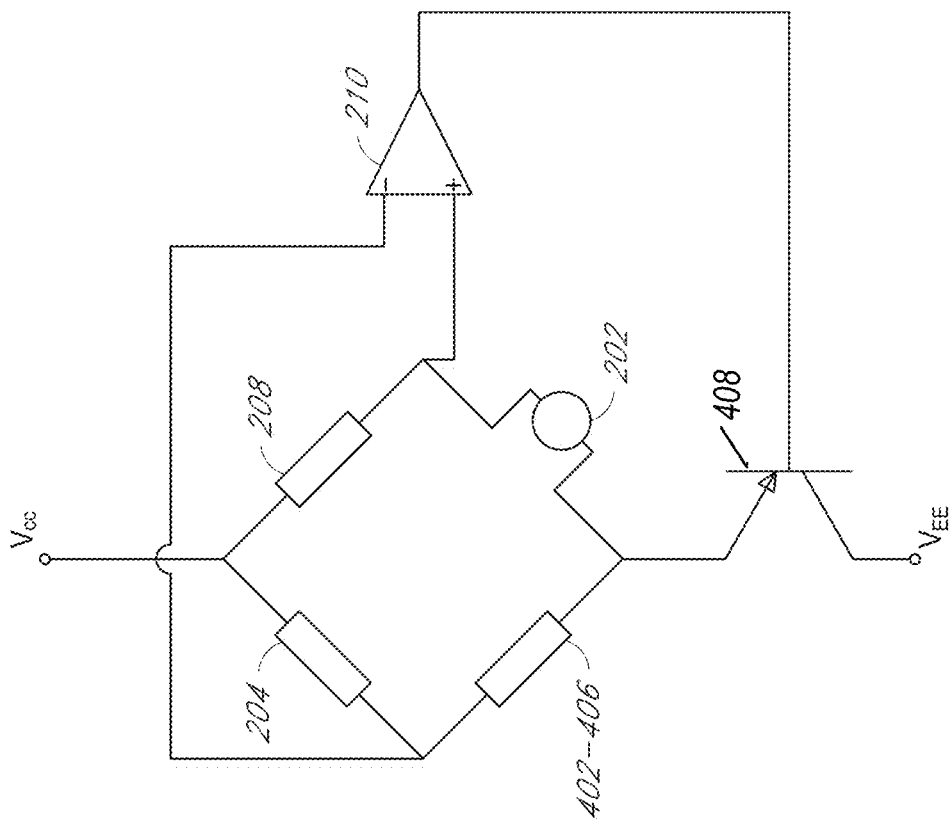
FIG. 4E illustrates an embodiment wherein the bridge is driven by a dual power supply.
Figure 4D:
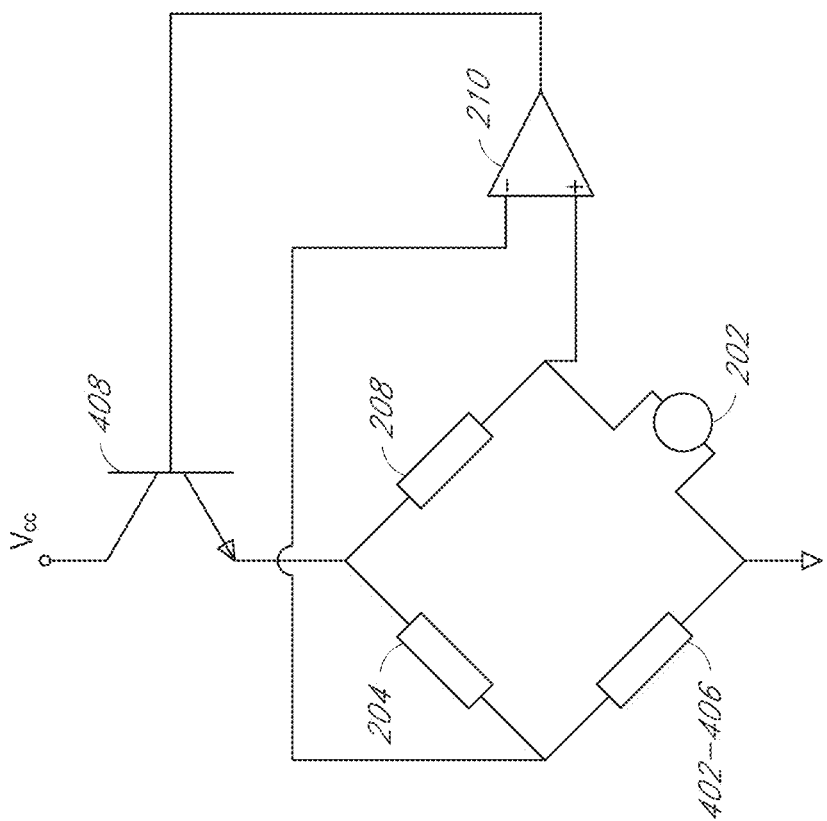
FIG. 4D illustrates another embodiment containing a buffer stage after the op-amp.

FIG. 4D illustrates another embodiment containing a buffer stage 408 after the op-amp. In some embodiments, the buffer stage 408 (for example, an NPN transistor) may function to reduce the burden on the op-amp 210 and improve start-up performance (for example, where op-amp 210 alone is not able to initially power the bridge). The buffer stage 408 can improve start-up performance by reducing the current drawn during start-up on the op-amp. FIG. 4E illustrates an embodiment wherein the bridge is driven by a dual power supply, in accordance with some embodiments, which may allow for greater power to be achieved. The circuit may include a buffer stage 408 located between the voltage divider and the voltage supply Vcc and/or Vee, the gate of the buffer stage 408 being connected to an output of the op-amp 210. In some embodiments, other variations may be possible. For example, the buffer stage 408 may be a PNP transistor instead of an NPN transistor. In some embodiments, this may allow for higher powers to be reached, at the expense of stability.

In some embodiments, the controller may receive a temperature measurement from a temperature sensor (not shown) measuring a temperature of the gases flow. Based upon the received temperature, the controller determines which target temperature the thermistor circuit 400 should operate at (for example, by switching switch 406 on or off). For example, the thermistor circuit 400 may be operated at a first target temperature when the flow temperature is within a desirable range associated with the first target temperature. In some embodiments, the thermistor circuit 400 may switch operation to a second target temperature when the flow temperature is within a desirable range associated with the second target temperature.

During operation, the controller may read the output voltage across the thermistor flow sensor (for example, an output voltage of the thermistor circuit run through a differential op-amp and transmitted to an ADC port of the controller). Based upon the target temperature that the thermistor flow sensor is currently operating at, and a measured gases flow temperature, the controller can be configured to determine a flow rate of the gases flow.

Dual Temperature Thermistor Circuit Output Voltage Range

In some embodiments, the thermistor circuit 400 is configured to present the same range of voltages to the controller (and/or the differential op-amp circuit), regardless of which temperature mode the thermistor circuit is operating in. For example, the thermistor circuit may be configured to output a voltage between about 1V and about 38V, or between about 5V and about 15V, regardless of the target temperature the thermistor circuit is operating at, wherein about 5V corresponds to a low flow and about 15V corresponds to a high flow. The voltage may then be scaled and/or shifted using the differential op-amp circuit to a second voltage range (for example, between about 0V and about 5V, or between about 0V and about 3.3V) that can be accepted by the controller.

Figure 5:
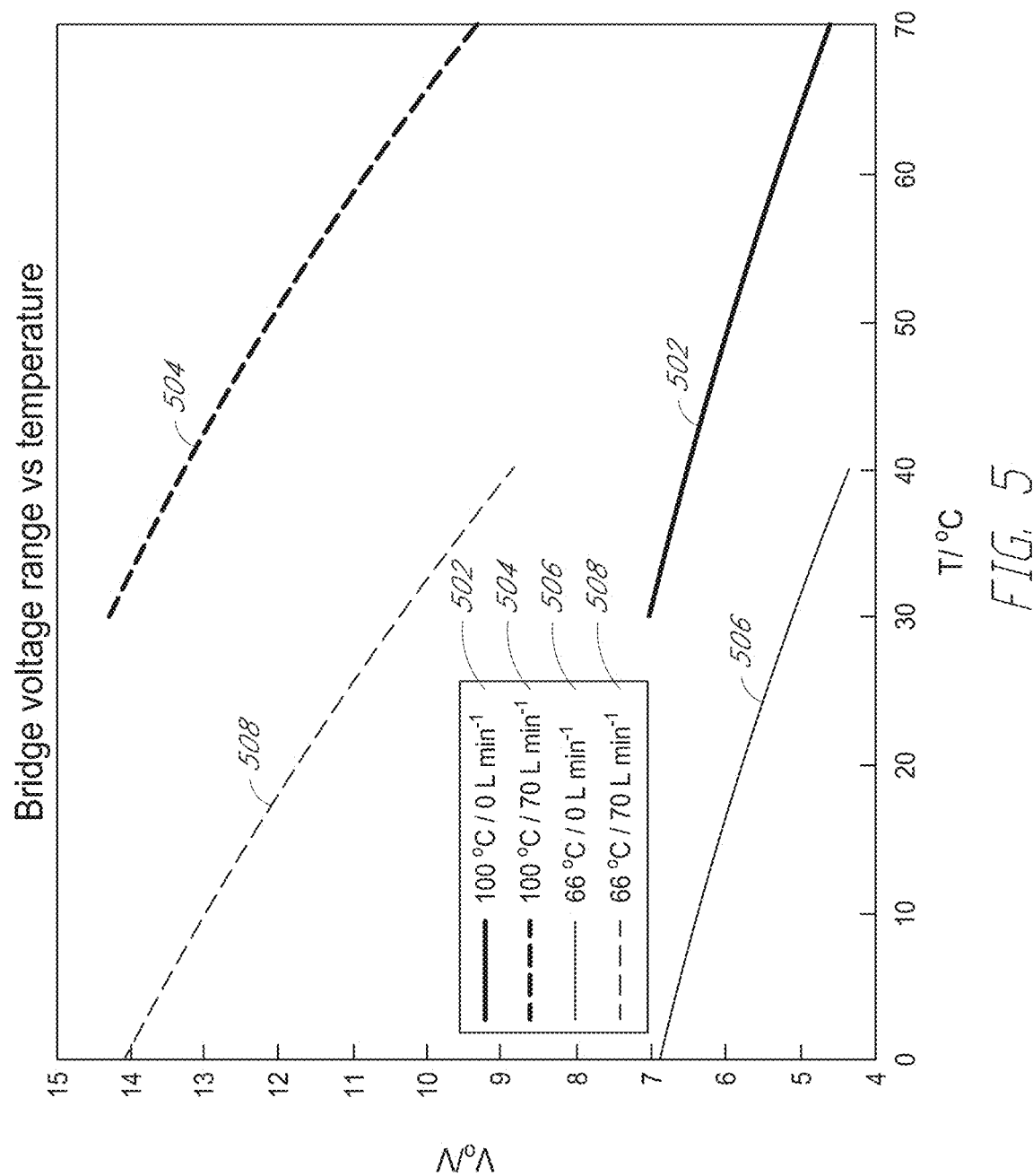
FIG. 5 illustrates a graph showing output voltage ranges for different temperatures and flow rates.

FIG. 5 illustrates a graph showing output voltage ranges for different temperatures and flow rates. Graph 500 includes a curve 502 illustrating an example relationship between flow temperature and thermistor circuit output voltage for a flow rate of 0 L/min for a target temperature of 100° C. Graph 500 includes a curve 504 illustrating an example relationship between flow temperature and thermistor circuit output voltage for a flow rate of 70 L/min for a target temperature of 100° C. Graph 500 includes a curve 506 illustrating an example relationship between flow temperature and thermistor circuit output voltage for a flow rate of 0 L/min for a target temperature of 66° C. Graph 500 includes a curve 508 illustrating an example relationship between flow temperature and thermistor circuit output voltage for a flow rate of 70 L/min for a target temperature of 66° C. As illustrated by comparing the curves 502 and 506, and/or the curves 504 and 508, for a given flow rate, the output voltage of the thermistor circuit can be substantially the same for the different target temperatures, when the difference between the flow temperature and the target temperature is the same. As such, the range of possible output voltages for the thermistor circuit can remain substantially the same, regardless of which target temperature the thermistor circuit is operating in.

Figure 6:
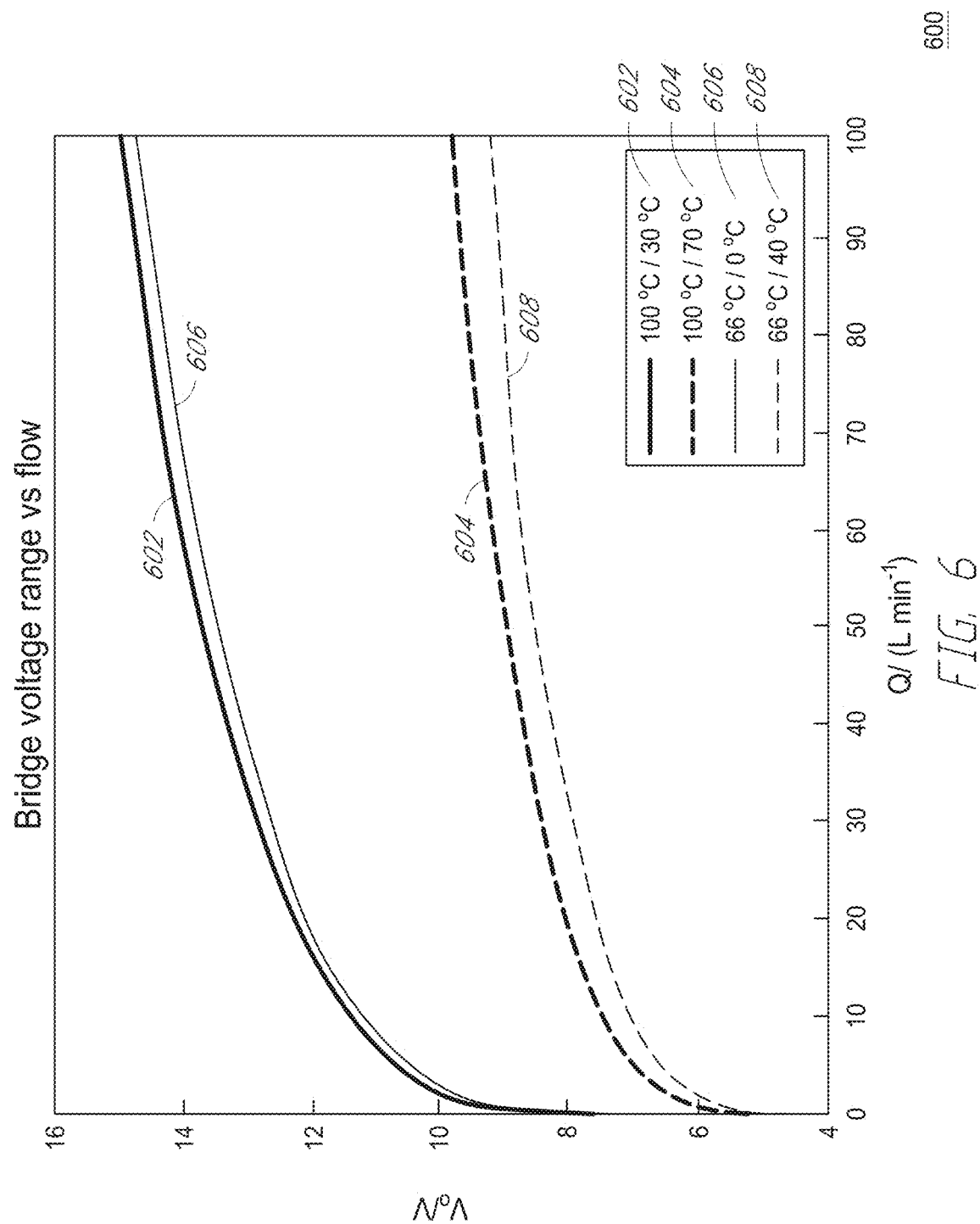
FIG. 6 illustrates a graph showing relationships between thermistor circuit output voltage and flow rate for different target temperature and flow temperature combinations.

FIG. 6 illustrates a graph 600 illustrating relationships between thermistor circuit output voltage and flow rate for different target temperature and flow temperature combinations. As shown in FIG. 6, a curve 602 illustrates an example relationship of the thermistor circuit output voltage and flow rate for a thermistor target temperature of 100° C. and a gases flow temperature of 30° C. A curve 604 illustrates an example relationship of the thermistor circuit output voltage and flow rate for a thermistor target temperature of 100° C. and a gases flow temperature of 70° C. A curve 606 illustrates an example relationship of the thermistor circuit output voltage and flow rate for a thermistor target temperature of 66° C. and a gases flow temperature of 0° C. A curve 608 illustrates an example relationship of the thermistor circuit output voltage and flow rate for a thermistor target temperature of 66° C. and a gases flow temperature of 40° C. gases flow As illustrated in graph 600, the relationship between output voltage and flow rate can be substantially similar for similar differences between target temperature and flow temperature, regardless of which target temperature the thermistor circuit is operating in. For example, the curves 602 and 606 can illustrate example relationships of the thermistor circuit output voltage and flow rate when the differences between target temperature and flow temperature are 70° C. and 66° C., respectively. The curves 602 and 606 can illustrate substantially similar output voltage values with respect to changes in the flow rate. The curves 604 and 608 can illustrate example relationships of the thermistor circuit output voltage and flow rate when the differences between target temperature and flow temperature are 30° C. and 26° C., respectively. The curves 604 and 608 can illustrate substantially similar output voltage values with respect to changes in the flow rate. The controller may compare the target temperature with the gases flow temperature (for example, using a comparator circuit), and use the difference to determine the flow rate based upon the received voltage from the thermistor flow sensor, regardless of the target temperature the thermistor flow sensor is operating in.

In some embodiments, configuring a thermistor circuit to present the same voltage range regardless of the operating target temperature may be accomplished through proper configuration of resistor values of the thermistor circuit (for example, resistors 204, 208, 402, and 404, as illustrated in FIG. 4A). Because the thermistor 202 is held at a constant target temperature during operation, the power input (due to electrical power) of the thermistor circuit 400 can be equal to the power output (from power losses). In some embodiments, the power loss due to the cooling flow can be determined based on King's law, which may be expressed as:

$$P_{loss} = (a + bQ^c)(T_s - T_a)$$

where a, b, and c are constants relating to the flow, $Q$ indicates the gases flow rate, and $T_s$ is the target temperature of the thermistor 202, and $T_a$ is the temperature of the gases flow.

The power input (for example, power consumed to heat the thermistor 202) may be expressed as:

$$P_{input} = \frac{V_s^2}{R_s}$$

where $V_s$ is the voltage across the thermistor 202, and $R_s$ is the resistance of the thermistor 202. Because the power input and power loss are equal, the voltage across the thermistor 202 $V_s$ can be expressed as:

$$V_s = \sqrt{(a + bQ^c)(T_s - T_a)R_s}$$

In addition, due to the thermistor 202 being part of a voltage divider, the voltage across the thermistor 202 $V_s$ can also be expressed as:

$$V_s = V_b \left( \frac{R_s}{R_b + R_s} \right)$$

As such, the relationship between voltage $V_b$, gases flow rate $Q$, and resistances of thermistor 202 and resistor 208 of the thermistor circuit can be expressed as:

$$V_b = \left(1 + \frac{R_b}{R_s}\right)\sqrt{(a + bQ^c)(T_s - T_a)R_s}$$

The resistance of the thermistor 202 $R_s$ may have different known values based upon the desired target temperatures $T_s$. Therefore, resistance $R_b$ of resistor 208 may be configured to determine the possible values of voltage $V_b$.

In order for the range of voltages $V_b$ to be the same regardless of which target temperature the thermistor circuit 400 is operating in, the value of $V_b$ should be the same value for the same flow rate in either target temperature scenario, which may be expressed as:

$$\left(1 + \frac{R_b}{R_{s,1}}\right)\sqrt{(a + bQ^c)(T_{s,1} - T_{a,1})R_{s,1}} =$$

$$\left(1 + \frac{R_b}{R_{s,2}}\right)\sqrt{(a + bQ^c)(T_{s,2} - T_{a,2})R_{s,2}}$$

which may be simplified to:

$$\left(1 + \frac{R_b}{R_{s,1}}\right)\sqrt{(T_{s,1} - T_{a,1})R_{s,1}} = \left(1 + \frac{R_b}{R_{s,2}}\right)\sqrt{(T_{s,2} - T_{a,2})R_{s,2}}$$

The expression $(T_{s,x} - T_{a,x})$ may represent a gases flow temperature range to be associated with each target temperature, wherein $T_{s,x}$ corresponds to a thermistor target temperature (for example, two different possible values, where the thermistor circuit is configured to operate at one of two different target temperatures), while $T_{a,x}$ corresponds to the gases flow temperature. In some embodiments, the thermistor circuit may be configured that when there is the same difference between the thermistor target temperature and gases flow temperature, the output voltage $V_b$ of the thermistor circuit should be the same, regardless of the target temperature mode that the thermistor circuit is currently operating in. As such, when $(T_{s,1} - T_{a,1}) = (T_{s,2} - T_{a,2})$, then:

$$\left(1 + \frac{R_b}{R_{s,1}}\right)\sqrt{R_{s,1}} = \left(1 + \frac{R_b}{R_{s,2}}\right)\sqrt{R_{s,2}}$$

Thus, a resistance $R_b$ for resistor 208 can be determined as a geometric mean of the resistance values $R_{s,1}$ and $R_{s,2}$ corresponding to the different target temperatures, as follows:

$$R_b = \sqrt{R_{s,1} \times R_{s,2}}$$

As discussed above, $R_{s,1}$ and $R_{s,2}$ can be defined by the values of the thermistor target temperature. For example, in a particular embodiment, the thermistor target temperatures may be about 66° C. and about 100° C., with corresponding resistances $R_{s,1}$ and $R_{s,2}$ being about 550Ω and about 220Ω, respectively. As such, the resistance $R_b$ can be set to about 350Ω (or about 330Ω, which can correspond to the closest resistance value in the E12 series of resistors).

In addition, because the voltages on the first and second voltage dividers of the thermistor circuit 400 are equal ($e_1 = e_2$), the resistances $R_1$, $R_2a$, and $R_2b$ of resistors 204, 402, and 404 can be configured to match a ratio between the resistances of resistor 208 and thermistor 202 for the different thermistor target temperatures. In embodiments where resistors 402 and 404 are configured to be in series (such that resistor 404 may be switched out using switch 406):

$$\frac{R_1}{R_{2a} + R_{2b}} = \frac{R_b}{R_{s,1}}$$

$$\frac{R_1}{R_{2a}} = \frac{R_b}{R_{s,2}}$$

As mentioned above, in some embodiments where the target temperatures for the thermistor are about 66° C. and about 100° C., with corresponding resistances $R_{s,1}$ and $R_{s,2}$ of about 550Ω and about 220Ω, respectively, resistance $R_b$ of resistor 208 has a value of about 350Ω. Therefore, the ratio of $R_b/R_s$ can be approximately 3/5 at the first target temperature of about 66° C. The ratio of $R_b/R_s$ can be approximately 3/2 at the second target temperature of about 100° C. Consequently, appropriate values for resistances $R_1$, $R_2a$, and $R_2b$ of resistors 204, 402, and 404 can be determined. For example, the resistors 204, 402, and 404 may be configured to have resistances $R_1$, $R_2a$, and $R_2b$ of about 15 kΩ, about 10 kΩ, and about 15 kΩ, respectively.

Figure 7:
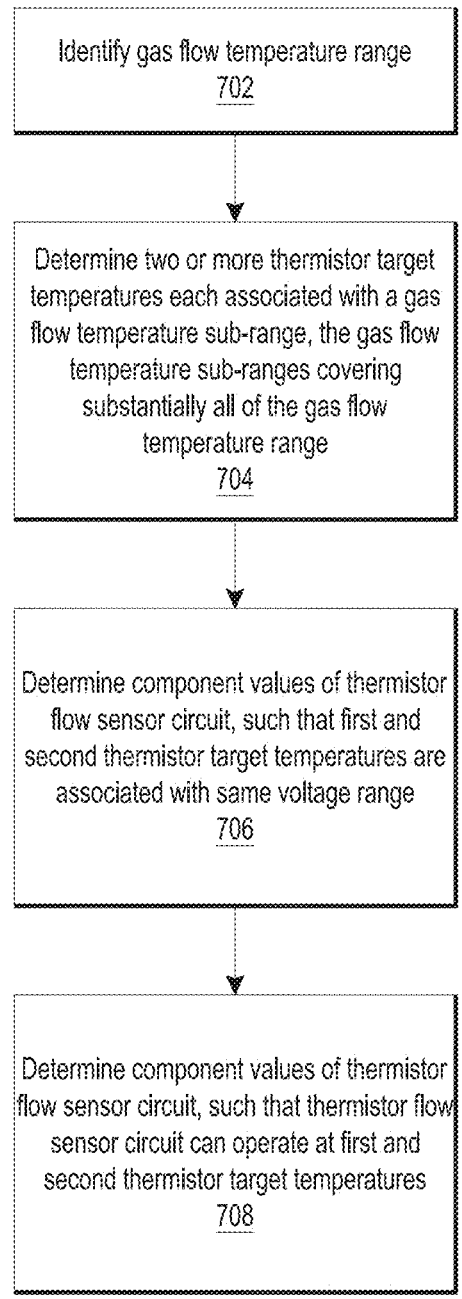
FIG. 7 illustrates a flowchart of a process for configuring a thermistor circuit of a thermistor flow sensor to be operable in at least a first target temperature and a second target temperature.

FIG. 7 illustrates a flowchart of an example process for configuring a thermistor circuit of a thermistor flow sensor to be operable in at least a first target temperature and a second target temperature. In some embodiments, the thermistor circuit may be configured to comprise first and second voltage dividers to provide first and second reference voltages to an op-amp (for example, as illustrated in FIG. 4A), allowing for the thermistor target temperature to be maintained.

At block 702, a gases flow temperature range may be identified. In some embodiments, different breathing therapy apparatuses may be associated with different gases flow temperature ranges. For example, a particular breathing therapy apparatus may be configured to produce a gases flow having a temperature of between about 0° C. and about 70° C.

At block 704, two or more thermistor target temperatures may be determined. Each thermistor target temperature may be associated with a desirable gases flow temperature sub-range, such that the gases flow temperature sub-ranges corresponding to the two or more thermistor target temperature ranges may cover substantially the entire temperature range identified at block 702. For example, where the identified gases flow temperature range is from about 0° C. to about 70° C., the one or more thermistor target temperatures may comprise a first thermistor target temperature of about 66° C. for a desirable gases flow temperature sub-range of between about 0° C. and about 40° C., and a second thermistor target temperature of about 100° C. for a desirable gases flow temperature sub-range of between about 30° C. and about 70° C. In some embodiments, the desired temperature sub-ranges of one or more thermistor target temperatures may overlap. The overlap may be done in order to prevent hysteresis, which is described in greater detail below.

In some embodiments, it is desirable for the output voltage range of the thermistor circuit to remain the same regardless of the thermistor target temperature the thermistor circuit is currently operating in. At block 706, one or more component values of the thermistor circuit may be determined such that each of the thermistor target temperatures may be associated with the same output voltage range. For example, in thermistor circuit 400 as illustrated in FIG. 4A, the output voltage range of the thermistor circuit 400 may be based upon the resistance $R_b$ of the resistor 208. As such, by setting the resistor 208 to an appropriate value as described above, the range of output voltages $V_b$ may be set to be substantially the same regardless of which target temperature the thermistor circuit 400 is operating in.

At block 708, one or more component values of the thermistor circuit may be determined such that the thermistor circuit is able to operate at the determined thermistor target temperatures. For example, where the thermistor circuit maintains a thermistor target temperature based upon one or more reference voltages generated by one or more voltage dividers, the resistance values of one or more resistors of the voltage dividers may be set to have a ratio that substantially matches a ratio associated with the thermistor at a given thermistor target temperature. For example, in the thermistor circuit 400 illustrated in FIG. 4A, one or more ratios between the resistances of the thermistor 202 and the resistor 208 may be determined for different desired target temperatures of the thermistor. The resistances of the resistors 204, 402, and 404 may then be set in order to substantially match the ratios associated with the desired target temperatures, allowing the thermistor circuit 400 to operate at the desired thermistor target temperatures.

Gases Flow Temperature Ranges and Hysteresis

As discussed above, the thermistor circuit (for example, thermistor circuit 400) may be configured to operate in multiple different thermistor target temperatures, each thermistor target temperature associated with a different gases flow temperature sub-range. In some embodiments, in order to avoid rapid switching between different thermistor target temperature modes if the gases flow temperature is close to a transition point between the different gases flow temperature sub-ranges, the gases flow temperature sub-ranges may overlap. For example, the thermistor circuit may be configured to operate at a low target temperature and a high target temperature corresponding to a low gases flow temperature sub-range and a high gases flow temperature sub-range, respectively. The upper bound of the low gases flow temperature sub-range may be higher than the lower bound of the high gases flow temperature sub-range. As such, when the thermistor is operating at the low target temperature, it is only switched to operate at the high target temperature if the measured gases flow temperature exceeds the upper bound of the low gases flow temperature sub-range. On the other hand, when the thermistor is operating at the high target temperature, it is only switched to operate at the low target temperature if the measured gases flow temperature decreases to less than the lower bound of the high gases flow temperature sub-range.

As an example, if the thermistor target temperatures are set at about 66° C. and about 100° C., with corresponding gases flow temperature sub-ranges of about 0° C.-about 40° C. and about 30° C.-about 70° C., respectively, the thermistor may switch from operating at about 66° C. to about 100° C. if the measured gases flow temperature exceeds about 40° C., and may switch from operating at about 100° C. to about 66° C. if the measured gases flow temperature is less than about 30° C. In some embodiments, switching between thermistor target temperatures may be triggered on a temperature change interrupt, a scheduled timer interrupt, and/or the like.

In some embodiments, switching between different thermistor target temperature modes may be restricted based upon a timer, which may be used to prevent a switch between different thermistor target temperature modes within a predetermined period of time.

Other Implementations

While FIG. 4A illustrates a thermistor circuit where the target temperature is controlled by switching a resistor (for example, resistor 404) in or out of a voltage bridge to control a reference voltage of the voltage bridge, it is understood that in other embodiments, the temperature of the thermistor (for example, the thermistor 202) of a thermistor flow sensor may be controlled by other methods. For example, in some embodiments, a switchable resistor may be added in series to the resistor 204 instead of the resistor 402. In some embodiments, a switchable resistor may be added in series to the resistor 208 or to the thermistor 202. In some embodiments, the switchable resistor may be added in parallel to one of the resistors of the thermistor circuit, instead of in series.

In some embodiments, the thermistor circuit may provide a different voltage output range depending upon the target temperature the thermistor circuit is operating in. The differential op-amp circuit (for example, as illustrated in FIG. 3) may be configured to scale, attenuate, and/or shift the output voltage of the thermistor circuit to produce a voltage output having a range that is substantially the same regardless of the target temperature mode. For example, resistors associated with the differential op-amp circuit may be switched in or out (for example, connected or bypassed) in response to a target temperature mode switch, in order to adjust the scaling and/or shifting performed by the differential op-amp circuit, such that the voltage range will be same regardless of the target temperature mode.

Process Flow

Figure 8:
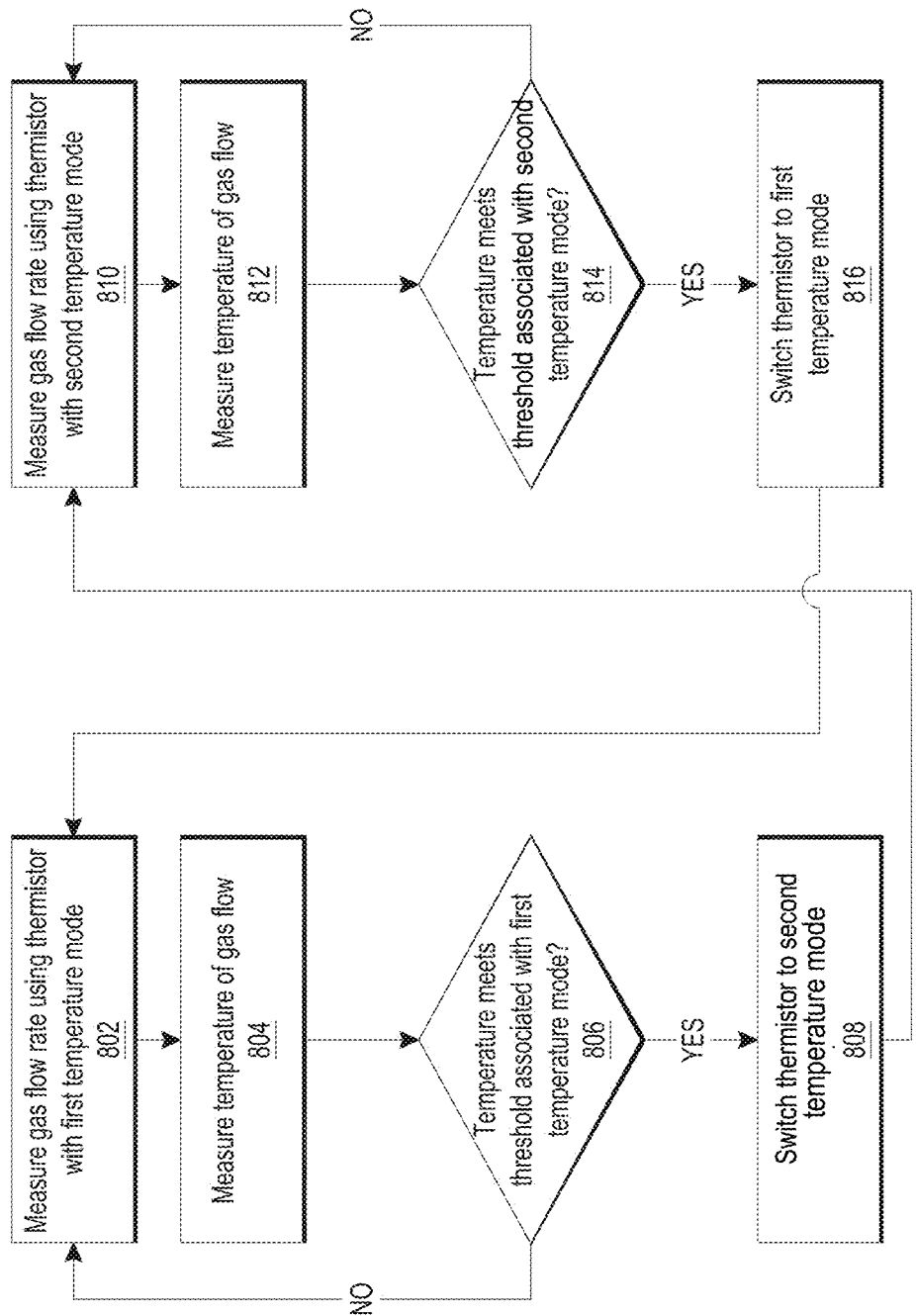
FIG. 8 illustrates a flowchart of a process for operating a thermistor flow sensor capable of operating at two different target temperatures, in accordance with some embodiments.

FIG. 8 illustrates a flowchart of an example process for operating a thermistor flow sensor capable of operating at two different target temperatures, in accordance with some embodiments. At block 802, a thermistor flow sensor may be operated at a first thermistor target temperature to measure a gases flow rate. For example, in an embodiment where the thermistor flow sensor is configured to operate at either about 66° C. or about 100° C., the first target temperature may correspond to about 66° C.

At block 804, a temperature of the gases flow may be measured. In some embodiments, the gases flow temperature may be measured periodically by a temperature sensor separate from the thermistor flow sensor. At block 806, a controller (such as the controller 13 in FIG. 1A) may determine whether the measured gases flow temperature satisfies a threshold values associated with the first thermistor target temperature. For example, in an embodiment where the first thermistor target temperature corresponds to about 66° C., to the controller may determine whether the gases flow temperature is greater than about 40° C. If the controller determines that the gases flow temperature does not satisfy the threshold value associated with the first thermistor target temperature, the process may return to block 802, where the thermistor flow sensor may continue to be operated at the first thermistor target temperature.

If the measured gases flow temperature satisfies the threshold, at block 808, the thermistor flow sensor may be switched to operate at a second thermistor target temperature. In some embodiments, switching the thermistor flow sensor between the first and second thermistor target temperatures may comprise connecting or disconnecting, mechanically or electronically, a resistor from a voltage bridge, to change a reference voltage of a voltage bridge within the thermistor flow sensor. In some embodiments, the reference voltage is configured such that the thermistor may be maintained at the first or second thermistor target temperature, depending on whether the resistor is connected or disconnected.

At block 810, the thermistor flow sensor may be used to measure gases flow rate while operating at the second thermistor target temperature. In some embodiments, the second thermistor target temperature may be about 100° C. At block 812, a temperature of the gases flow may be measured (for example, using the temperature sensor separate from the thermistor flow sensor).

At block 814, the controller may determine whether the measured gases flow temperature satisfies a threshold values associated with the second thermistor target temperature. In some embodiments, the threshold value may be different from the threshold associated with the first thermistor target temperature. For example, in an embodiment where the second thermistor target temperature corresponds to about 100° C., the gases flow temperature may be considered to satisfy the threshold value if it is less than about 30° C. As such, the threshold values associated with the first and second thermistor target temperatures may define overlapping temperature ranges. By having overlapping temperature ranges, hysteresis may be used to avoid rapid switching between the first and second thermistor target temperatures when the gases flow temperature is at a temperature near a transition point between different temperature ranges associated with the first and second thermistor target temperatures.

If the controller determines that the gases flow temperature does not satisfy the second threshold, the process may return to block 810, where the thermistor flow sensor may continue to measure the gases flow while operating at the second thermistor target temperature. If the gases flow temperature satisfies the second threshold, at block 816, the thermistor flow sensor may be switched to operate at the first thermistor target temperature. The process may then return to block 802, where the thermistor flow sensor may be used to measure the gases flow while operating at the first thermistor target temperature.

By using a thermistor flow sensor configured to operate at different thermistor target temperatures, resolution issues arising from the difference between the gases flow temperature and the thermistor target temperature being too large or too small may be alleviated. By configuring the thermistor flow sensor to be able to return substantially the same voltage range regardless of which target temperature the thermistor flow sensor is operating in, substantially all of the voltage range that can be accepted by the controller may be used. This may improve resolution of the thermistor flow sensor.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The terms "approximately," "about," and "substantially" as used herein represent an amount close to the stated amount that still performs a desired function or achieves a desired result. For example, in some embodiments, as the context may permit, the terms "approximately", "about", and "substantially" may refer to an amount that is within less than or equal to 10% of, within less than or equal to 5% of, and within less than or equal to 1% of the stated amount.

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

Depending on the embodiment, certain acts, events, or functions of any of the algorithms, methods, or processes described herein can be performed in a different sequence, can be added, merged, or left out altogether (for example, not all described acts or events are necessary for the practice of the algorithms). Moreover, in certain embodiments, acts or events can be performed concurrently, for example, through multi-threaded processing, interrupt processing, or multiple processors or processor cores or on other parallel architectures, rather than sequentially.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. A breathing assistance apparatus that provides a flow of gases to a patient, the breathing assistance apparatus comprising:
   at least one gases flow path configured to direct the flow of gases to the patient;
   a gases flow inlet configured to receive the flow of gases from a gases flow source;
   a temperature sensor configured to measure a temperature of the flow of gases; and
   a gases flow rate sensing system configured to measure a gases flow rate of the flow of gases, wherein the gases flow rate sensing system is configured to operate in at least two different temperature modes based upon the measured temperature of the flow of gases.

2. The breathing assistance apparatus of claim 1, wherein the gases flow source comprises a blower.

3. The breathing assistance apparatus of claim 2, wherein the temperature sensor, the gases flow rate sensing system, or both the temperature sensor and the gases flow rate sensing system are upstream of the blower.

4. The apparatus of claim 2, wherein the temperature sensor, the gases flow rate sensing system, or both the temperature sensor and the gases flow rate sensing system are disposed within a sensor assembly having a housing, the sensor assembly located in a sensor zone within an inlet flow path upstream of the blower.

5. The breathing assistance apparatus of claim 2, wherein the temperature sensor, the gases flow rate sensing system, or both the temperature sensor and the gases flow rate sensing system are downstream of the blower.

6. The apparatus of claim 2, wherein the blower is comprised within a blower/sensor module.

7. The apparatus of claim 6, wherein the blower/sensor module is removable and configured for insertion into a housing of the apparatus.

8. The apparatus of claim 6, wherein the blower/sensor module is non-removable and configured for insertion into a housing of the apparatus.

9. The apparatus of claim 6, wherein the blower/sensor module comprises a sensing circuit board.

10. The apparatus of claim 9, wherein at least a portion of the gases flow rate sensing system is on or within the sensing circuit board.

11. The breathing assistance apparatus of claim 1, wherein the breathing assistance apparatus is a Continuous Positive Airway Pressure (CPAP) apparatus, or an apparatus that delivers a noninvasive ventilation (NIV) flow, or an apparatus that delivers a nasal high flow (NHF) flow of gases.

12. The breathing assistance apparatus of claim 1, comprising a humidifier.

13. The breathing assistance apparatus of claim 1, wherein the at least one gases flow path comprises a heated respiratory tube.

14. The breathing assistance apparatus of claim 1, further comprising a face mask, a nasal mask, a nasal pillows mask, a tracheostomy interface, a nasal cannula, or an endotracheal tube.

15. The breathing assistance apparatus of claim 1, wherein the gases flow rate sensing system is configured to operate in more than two different temperature modes.

16. A breathing assistance apparatus that provides a flow of gases to a patient, the breathing assistance apparatus comprising:
   at least one gases flow path configured to direct the flow of gases from a gases flow source;
   a gases flow inlet configured to receive the flow of gases from a gases flow source;
   a temperature sensor configured to measure a temperature of the flow of gases; and
   a gases flow rate sensing system configured to measure a gases flow rate of the flow of gases,
      wherein the gases flow rate sensing system is configured to operate in at least two different temperature modes based upon the measured temperature of the flow of gases,
      wherein the gases flow rate sensing system comprises a thermistor circuit, and
      wherein the thermistor circuit comprises a voltage divider comprising at least a first arm and a second arm.

17. The breathing assistance apparatus of claim 16, wherein the gases flow rate sensing system is configured to change from a first temperature mode to a second temperature mode in response to the measured temperature of the flow of gases meeting a predetermined threshold.

18. The breathing assistance apparatus of claim 17, wherein changing a target temperature mode of the thermistor circuit comprises changing a resistance value associated with the first arm of the voltage divider.

19. The breathing assistance apparatus of claim 18, wherein changing the resistance value associated with the first arm of the voltage divider comprises connecting a resistor of the first arm of the voltage divider.

20. The breathing assistance apparatus of claim 18, wherein changing the resistance value associated with the first arm of the voltage divider comprises bypassing a resistor of the first arm of the voltage divider.

21. The breathing assistance apparatus of claim 17, further comprising a buffer stage between the voltage divider and a power supply.

22. The breathing assistance apparatus of claim 21, wherein the buffer stage comprises a transistor.

23. The breathing assistance apparatus of claim 17, wherein the voltage divider is driven by dual power supplies.

* * * * *